(12) United States Patent
Guthrie

(10) Patent No.: US 8,029,479 B2
(45) Date of Patent: Oct. 4, 2011

(54) BANDAGE WITH CATHETER PORT POCKET

(76) Inventor: Gertrude T. Guthrie, Cambridge, MD (US)

( * ) Notice: Subject to any disclaimer, the term of this patent is extended or adjusted under 35 U.S.C. 154(b) by 189 days.

(21) Appl. No.: 12/213,452

(22) Filed: Jun. 19, 2008

(65) Prior Publication Data

US 2009/0318874 A1 Dec. 24, 2009

(51) Int. Cl.
*A61M 5/32* (2006.01)

(52) U.S. Cl. ... 604/180; 604/174; 604/179; 128/DIG. 6; 128/DIG. 26

(58) Field of Classification Search ............. 128/DIG. 6, 128/DIG. 26; 602/54; 604/174, 177, 179, 604/180, 48, 93.01, 176, 178, 175
See application file for complete search history.

(56) References Cited

U.S. PATENT DOCUMENTS

| | | | |
|---|---|---|---|
| 4,122,857 A | 10/1978 | Haerr | |
| 4,324,237 A * | 4/1982 | Buttaravoli | 602/54 |
| 4,449,975 A | 5/1984 | Perry | |
| 4,583,976 A * | 4/1986 | Ferguson | 604/174 |
| 4,666,432 A | 5/1987 | McNeish | |
| 4,743,232 A | 5/1988 | Kruger | |
| 4,751,133 A * | 6/1988 | Szycher et al. | 442/1 |
| 4,941,882 A | 7/1990 | Ward et al. | |
| 5,035,687 A | 7/1991 | Sandbank | |
| 5,344,415 A | 9/1994 | DeBusk et al. | |
| 5,372,589 A | 12/1994 | Davis | |
| 6,770,793 B2 * | 8/2004 | Brooks | 602/48 |
| 6,827,706 B2 * | 12/2004 | Tollini | 604/180 |
| 2002/0156423 A1 * | 10/2002 | Tollini | 604/180 |
| 2003/0216694 A1 | 11/2003 | Tollini | |

OTHER PUBLICATIONS

Notification of Transmittal of the International Search Report (Forms PCT/ISA/220 and PCT/ISA/210) and the Written Opinion of the International Searching Authority (Form PCT/ISA/237) issued in the corresponding International Application No. PCT/US2009/003563 dated Jan. 20, 2010.

* cited by examiner

*Primary Examiner* — Kevin C Sirmons
*Assistant Examiner* — Shefali Patel
(74) *Attorney, Agent, or Firm* — Buchanan Ingersoll & Rooney PC

(57) ABSTRACT

An intravenous bandage having a first component defining an adhesive area for attaching the intravenous bandage to a patient and a second component secured to the first component so as to define a port pocket therebetween for providing stability and sterility to a catheter lumen.

18 Claims, 4 Drawing Sheets

BANDAGE WITH CATHETER PORT POCKET

FIELD OF THE INVENTION

The present invention is directed to an intravenous bandage and more particularly, to an intravenous bandage having a port pocket for providing stability and sterility of the catheter lumens.

BACKGROUND OF THE INVENTION

In common practice, a catheter is affixed to a medical patient by use of an adhesive or surgical tape placed over the catheter atop the skin. Similarly, the hub between the catheter and cannula is also maintained in place by tape. A safety loop is typically formed in the catheter tubing to ensure that any tension applied to the catheter is not passed directly to the cannula, but instead is taken up in the slack of the safety loop. As expected, each of the several times this taping process is to be performed over the course of a given catheterization procedure, a considerable amount of the time of a medical practitioner is consumed. Furthermore, the frequent application and removal of typically strong adhesive tape regularly results in the excoriation of the skin underneath the tape and at the site of the cannula insertion. Difficulties attendant to removal and reapplication of tape in this context give practitioners incentives to change the tape less frequently, thereby causing increased incidence and severity of infection and skin suffocation.

When intravenous access by a central intravenous (IV) line is required over a prolonged period of time, as in the case of long term chemotherapy regimens, extended antibiotic therapy, long term treatment of children's' diseases, or total parenteral nutrition, the reapplication of tape becomes even more problematic. A central IV line flows through a catheter with its tip within a large vein, usually the superior vena cava or inferior vena cava, or within the right atrium of the heart. Moreover, the PICC line (peripherally inserted central catheter) is vulnerable to damage and occlusion from movement of the arm or of the line itself, or from pressure on the arm and the thin, sterile dressing maintaining the central IV must be protected.

Accordingly, it would be desirable to provide a stable and sterile bandaging for securing the catheter lumens of a central IV line, or any other type of catheter.

SUMMARY OF THE INVENTION

These and other objects are met by an intravenous bandage preferably having a first component defining an adhesive area for attaching the intravenous bandage to a patient, and a second component, the second component being secured to the first component so as to define a port pocket therebetween for receiving and providing stability and sterility to the catheter lumen ports. According to a further aspect of the invention, the first component comprises a first bandage portion and a first portion, said first portion being smaller in dimension than said first bandage portion and the second component comprises a second bandage portion and a second portion, the second portion being smaller in dimension than said second bandage portion.

In accordance with a further aspect of a preferred embodiment of the invention, an adhesive surface of the second portion is secured to an adhesive surface of the second bandage portion in overlapping fashion and an adhesive surface of said second bandage portion is aligned with and secured to a non-adhesive surface of the first bandage portion. Thus, the port pocket is defined between the non-adhesive surface of the second portion and the non-adhesive surface of the first bandage portion.

In accordance with a still further aspect of the preferred embodiment of the invention, the first component and the second component each include at least one piece of an adhesive tape, most preferably a silk adhesive tape.

BRIEF DESCRIPTION OF THE DRAWING FIGURES

These and other objects, features, and advantages of the present invention will become more readily apparent to those skilled in the art upon reading the following detailed description, in conjunction with the appended drawings in which.

DETAILED DESCRIPTION OF THE PREFERRED EMBODIMENTS

Figure 1:
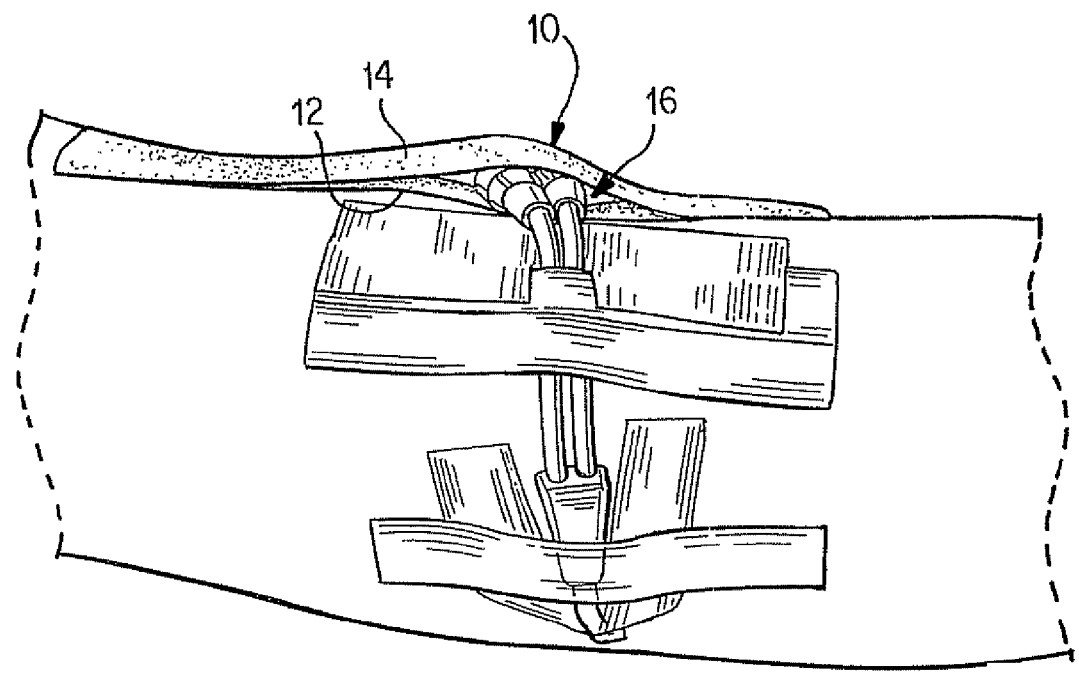
FIG. 1 is a perspective view of an intravenous bandage with a port pocket in accordance with a preferred embodiment of the present invention.
Figure 2:
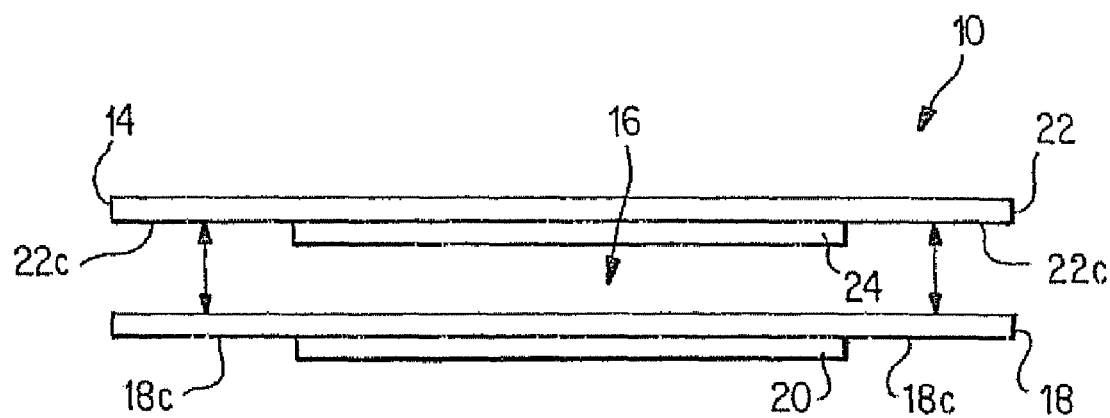
FIG. 2 is an exploded view of the intravenous bandage shown in FIG. 1.
Figure 3A:
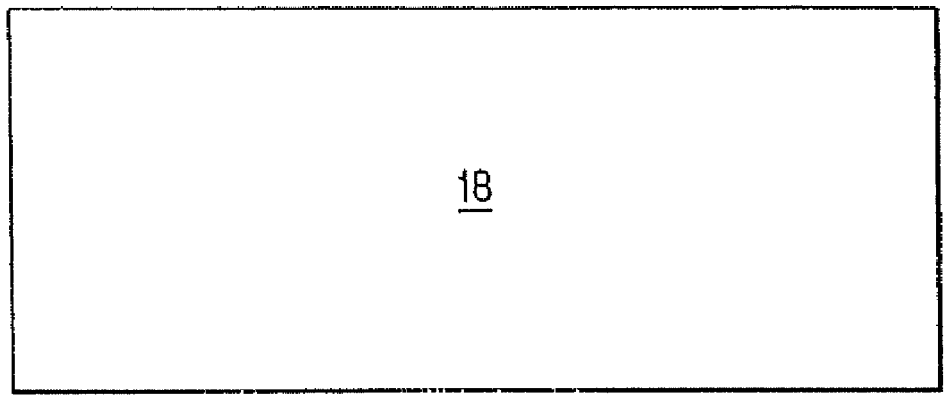
FIG. 3A is a top plan view of the first bandage portion of the intravenous bandage shown in FIG. 1.
Figure 3B:
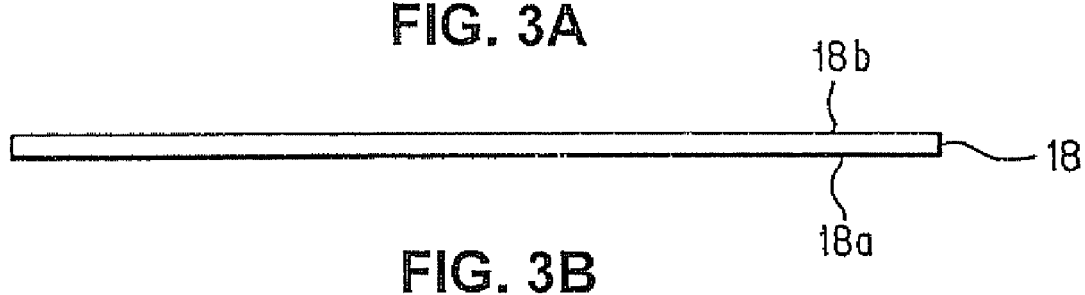
FIG. 3B is a side elevational view of the first bandage portion shown in FIG. 3A.
Figure 4A:
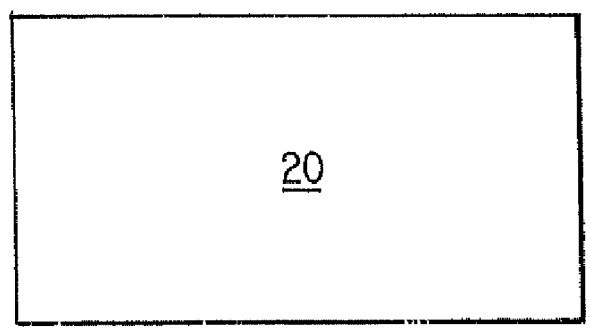
FIG. 4A is a top plan view of the first portion of the intravenous bandage shown in FIG. 1.
Figure 4B:
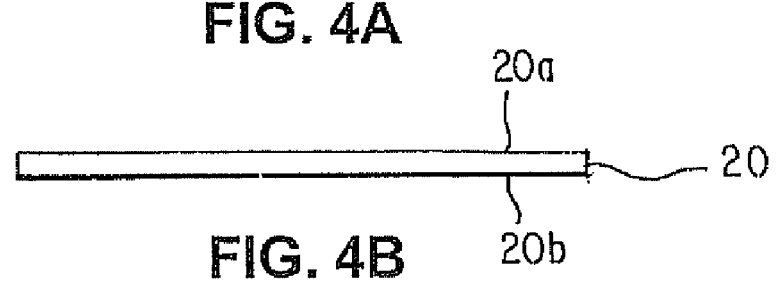
FIG. 4B is a side elevational view of the first portion shown in FIG. 4A.
Figure 5A:
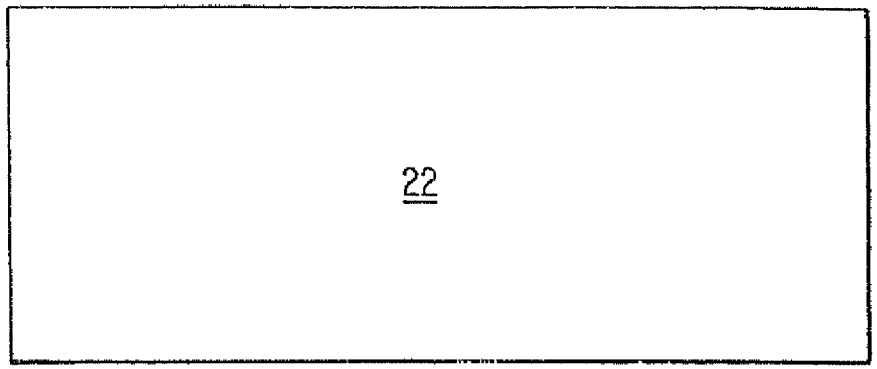
FIG. 5A is a top plan view of the second bandage portion of the intravenous bandage shown in FIG. 1.
Figure 5B:
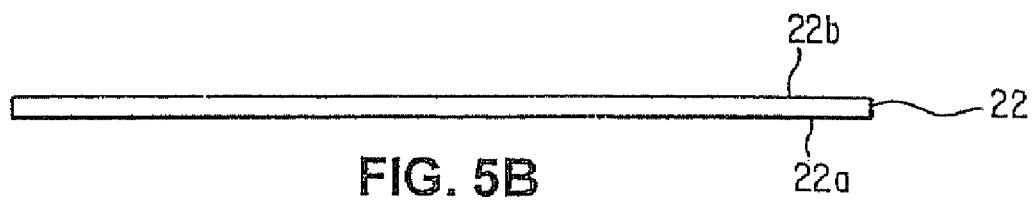
FIG. 5B is a side elevational view of the second bandage portion shown in FIG. 5A.
Figure 6A:
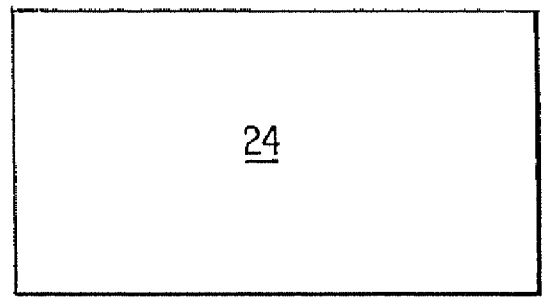
FIG. 6A is a top plan view of the second portion of the intravenous bandage shown in FIG. 1.
Figure 6B:
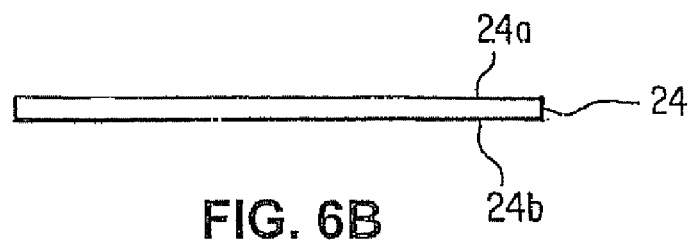
FIG. 6B is a side elevational view of the second portion shown in FIG. 6A.

Referring to FIGS. 1 and 2, an intravenous bandage in accordance with a preferred embodiment of the present invention is shown generally by reference numeral 10. The intravenous bandage 10 includes a first component 12 intended for attachment to the skin of a patient and a second component 14 secured to first component 12. A pocket 16 is defined between components 12 and 14 for receiving the head of the catheter lines and their single, double or multiple ports. Retention of the ports within the pocket 16 restricts the motion and prevents entanglement or jerking of the catheter line, thus protecting the integrity of the sterile dressing covering the insertion site. The intravenous bandage 10 also gives extra protection against the accidental severing or pulling out of catheter lines.

Referring also to FIGS. 3A, 3B, 4A and 4B, first component 12 includes a first bandage portion 18 and a first portion 20. First bandage portion 18 comprises a piece of adhesive tape, preferably a silk tape, and more preferably Durapore® Tape available from 3M Company, or any type of similar adhesive tape suitable for medical use. First bandage portion 18 has an adhesive surface 18a and an opposing non-adhesive surface 18b. First portion 20 similarly comprises a piece of adhesive tape of the same or different type as first bandage portion 18. First portion 20 similarly has an adhesive surface 20a and an opposing non-adhesive surface 20b. First portion 20 is smaller in size than first bandage portion 18. In a preferred embodiment, first portion 20 is adhered to first bandage portion 18 in a centered position, adhesive surface 20a being adhered to adhesive surface 18a such that only the edges 18c of the adhesive surface 18a of first bandage portion 18 remain exposed for securing the same to the skin of a patient.

Referring also to FIGS. 5A, 5B, 6A and 6B, second component 14 includes a second bandage portion 22 and a second portion 24. Second bandage portion 22 comprises a piece of adhesive tape, preferably a silk tape, and more preferably Durapore® Tape available from 3M Company, or any type of similar adhesive tape suitable for medical use. Second bandage portion 22 has an adhesive surface 22a and an opposing non-adhesive surface 22b. Second portion 24 similarly comprises a piece of adhesive tape of the same or different type as second bandage portion 22. Second portion 24 similarly has an adhesive surface 24a and an opposing non-adhesive surface 24b. Second portion 24 is smaller in size than second bandage portion 22. In a preferred embodiment, second portion 24 is adhered to second bandage portion 22 in a centered position, adhesive surface 24a being adhered to adhesive surface 22a such that only the edges 22c of the adhesive surface 22a of second bandage portion 22 remain exposed for securing the same to first component 12, as explained below.

In order to form intravenous bandage 10, second component 14 is adhered to first component 12 by securing the exposed edges 22c of adhesive surface 22a of second bandage portion 22 to the non-adhesive surface 18b of first bandage portion in an aligned overlapping fashion, as shown by the arrows in FIG. 2. In so doing, the second portion 24 of the second component 14, and more particularly, the non-adhesive surface 24b of the second portion 24 is facing the non-adhesive surface 18b of the first bandage portion 18 to thereby define the port pocket 16 therebetween. The port pocket 16 preferably has no exposed adhesive surfaces to inadvertently pull on the catheter lumens. The intravenous bandage 10 is applied to a patient by securing the exposed edges 18c of adhesive surface 18a to the skin of the patient proximate to the location of the ports for the catheter, as shown in FIG. 1, thus giving central line IV therapy protection and stability in an easy to use bandage.

Stability and sterility are major factors in the successful use of a PICC line or midline catheter. The unique design of the intravenous bandage 10 of the present invention offers security, and yet uses only two-fifths of the adhesive-to-skin contact area of conventional adhesive tapes of its size. Therefore there is less damage to the patient from daily or weekly removal of adhesive tapes. Preferably, first component 18 and second component 22 are approximately 5"×2" in size and first portion 20 and second portion 24 are between approximately 2"×2" and 2.5"×2" in size such the port pocket 16 formed therebetween will be either 3" wide for a double lumen catheter or 2.5" wide for a single lumen catheter. Other sizes and dimensions can of course also be used as would be apparent to one skilled in the art based upon the size and number of lumen ports to be stabilized.

It has been found that a clean, secure and viable intravenous bandage 10 can be left in place from PICC line dressing change to the following dressing change. A fresh intravenous bandage 10 will need to be placed in proper position for each new dressing, that is, positioned to allow the arc of the trailing ends of the lines and lumens to sweep into the pocket 16.

The intravenous bandage 10 contains no gauze to absorb liquid medications or flushes and thus does not harbor bacteria. An alcohol pad can be used to clean the skin under the center of the intravenous bandage 10, or to clean within the pocket 16 itself as necessary.

A central IV line can have one or more parallel lumens within the catheter in order to allow for different medications to be infused at the same time. After each infusion, the intravenous bandage 10 according to a preferred embodiment of the invention can be used to secure each of the one or more flushed lumens.

Central IV lines carry some risks of bleeding and bacterial infection. By using the intravenous bandage 10 to reduce the motion of the external connectors (i.e., double-lumen; two parallel compartments, each with its own external connector), or a single tube and connector (i.e, single-lumen), the patient can restrict the stress and wear on the sterile dressing covering the insertion site and thereby reduce the risk of bleeding and infection.

When treating young children (or patients not in control of their own actions) with Central IV lines, the intravenous bandage 10 also helps to restrict access to external lines and lumens. Stability and restriction of access are of great importance in maintaining the sterility and integrity of line and dressing.

In sum, the intravenous bandage 10 of the present invention allows a patient to lead a more normal life, gives protection to the IV line, external lines and lumens, and does this with a neat, small, more compact and comfortable profile.

Although certain preferred embodiments of the present invention have been shown and described in detail with respect to a central IV and/or PICC line catheter, it should be understood that various changes and modifications may be made therein for use with any type of catheter without departing from the scope of the appended claims.

What is claimed is:

1. A bandage comprising:
a first component defining an adhesive area for attaching the bandage to a patient; and
a second component;
said second component being independent from said first component;
wherein said second component is secured to said first component so as to define a port pocket therebetween;
wherein, when in use, said port pocket is defined between a non-adhesive surface of said first component, directly therebelow, and a non-adhesive surface of said second component, directly thereabove;
wherein said first component comprises a first bandage portion and a first portion, said first portion being smaller in dimension than said first bandage portion; and
wherein said second component comprises a second bandage portion and a second portion, said second portion being smaller in dimension than said second bandage portion.

2. The bandage of claim 1 wherein said first bandage portion includes an adhesive surface and an opposing non-adhesive surface, said opposing non-adhesive surface defining said non-adhesive surface of said first component.

3. The bandage of claim 2 wherein said second bandage portion includes an adhesive surface and an opposing non-adhesive surface.

4. The bandage of claim 3 wherein said first portion includes an adhesive surface and an opposing non-adhesive surface.

5. The bandage of claim 4 wherein said second portion includes an adhesive surface and an opposing non-adhesive surface, said opposing non-adhesive surface of said second portion defining said non-adhesive surface of said second component.

6. The bandage of claim 5 wherein said adhesive surface of said second portion is secured to said adhesive surface of said second bandage portion in overlapping fashion.

7. The bandage of claim 6 wherein said adhesive surface of said second bandage portion is aligned with and secured to said non-adhesive surface of said first bandage portion.

8. The bandage of claim 7 wherein said adhesive surface of said first portion is secured to said adhesive surface of said first bandage portion in overlapping fashion such that a portion of said adhesive surface of said first bandage portion remains exposed, said exposed portion defining the adhesive area of said first component for attaching the bandage to a patient.

9. The bandage of claim 8 wherein said port pocket is defined between said non-adhesive surface of said second portion and said non-adhesive surface of said first bandage portion.

10. The bandage of claim 1 wherein said first component comprises at least one piece of an adhesive tape.

11. The bandage of claim 10 wherein said second component comprises at least one piece of adhesive tape.

12. The bandage of claim 11 wherein said adhesive tape comprises a silk tape.

13. The bandage of claim 1 wherein neither said first component nor said second component includes an absorbent gauze material.

14. A bandage comprising:
   a first component having an adhesive area for attaching the bandage to a patient; and
   a second component;
   said first component and said second component each having opposing longitudinal edges, said second component being secured to said first component only along said opposing longitudinal edges so as to define a port pocket;
   wherein, when in use, said port pocket is defined between a non-adhering surface of said second component and a non-adhering surface of said first component and configured to removably receive an end of at least one catheter line port.

15. The bandage of claim 14 wherein said first component comprises a first bandage portion and a first portion, said first portion being smaller in dimension than said first bandage portion, and wherein said second component comprises a second bandage portion and a second portion, said second portion being smaller in dimension than said second bandage portion.

16. The bandage of claim 15 wherein said first bandage portion includes an adhesive surface and an opposing non-adhesive surface, said opposing non-adhesive surface defining said non-adhesive surface of said first component and wherein said second portion includes an adhesive surface and an opposing non-adhesive surface, said opposing non-adhesive surface of said second portion defining said non-adhesive surface of said second component.

17. The bandage of claim 16 wherein said second bandage portion includes an adhesive surface and an opposing non-adhesive surface and said first portion includes an adhesive surface and an opposing non-adhesive surface, said adhesive surface of said first portion is secured to said adhesive surface of said first bandage portion in overlapping fashion such that a portion of said adhesive surface of said first bandage portion remains exposed, said exposed portion defining the adhesive area of said first component for attaching the bandage to a patient.

18. The bandage of claim 17 wherein said port pocket is defined between said non-adhesive surface of said second portion and said non-adhesive surface of said first bandage portion.

* * * * *